(12) United States Patent
Heinemann et al.

(10) Patent No.: US 6,632,817 B2
(45) Date of Patent: Oct. 14, 2003

(54) FLUOROMETHOXIMINO COMPOUNDS

(76) Inventors: Ulrich Heinemann, c/o Bayer Aktiengesellschaft, D 51368 Leverkusen (DE); Herbert Gayer, c/o Bayer Aktiengesellschaft, D 51368 Leverkusen (DE); Peter Gerdes, c/o Bayer Aktiengesellschaft, D 51368 Leverkusen (DE); Albrecht Marhold, c/o Bayer Aktiengesellschaft, D 51368 Leverkusen (DE); Uwe Stelzer, c/o Bayer Aktiengesellschaft, D 51368 Leverkusen (DE); Reinhard Lantzsch, c/o Bayer Aktiengesellschaft, D 51368 Leverkusen (DE); Ralf Tiemann, c/o Bayer Aktiengesellschaft, D 51368 Leverkusen (DE); Klaus Stenzel, c/o Bayer Aktiengesellschaft, D 51368 Leverkusen (DE); Astrid Mauler-Machnik, c/o Bayer Aktiengesellschaft, D 51368 Leverkusen (DE); Stefan Dutzmann, c/o Bayer Aktiengesellschaft, D 51368 Leverkusen (DE); Martin Kugler, c/o Bayer Aktiengesellschaft, D 51368 Leverkusen (DE); Hans-Ulrich Buschhaus, c/o Bayer Aktiengesellschaft, D 51368 Leverkusen (DE)

( * ) Notice: Subject to any disclaimer, the term of this patent is extended or adjusted under 35 U.S.C. 154(b) by 0 days.

(21) Appl. No.: 09/933,208

(22) Filed: Aug. 20, 2001

(65) Prior Publication Data

US 2002/0028811 A1 Mar. 7, 2002

Related U.S. Application Data

(62) Division of application No. 09/455,084, filed as application No. PCT/EP98/03038 on May 22, 1998, now Pat. No. 6,306,855.

(30) Foreign Application Priority Data

Jun. 3, 1997 (DE) .......................... 197 23 195

(51) Int. Cl.[7] .................. C07D 251/12; C07D 239/32; C07D 271/07; C07D 285/08; A01N 43/836

(52) U.S. Cl. .................. 514/241; 514/256; 514/269; 514/361; 544/216; 544/315; 549/129; 549/132; 560/8

(58) Field of Search .................. 544/216, 315; 548/129, 132; 560/8; 514/241, 256, 269, 361

(56) References Cited

U.S. PATENT DOCUMENTS

| 5,070,193 A | 12/1991 | Schundehutte et al. ..... 540/125 |
|---|---|---|
| 5,206,245 A | 4/1993 | Clough et al. ............... 514/269 |
| 5,977,123 A | 11/1999 | Gerdes et al. ............... 514/269 |
| 6,031,107 A | 2/2000 | Heinemann et al. ........ 548/129 |
| 6,306,855 B1 | 10/2001 | Heinemann et al. ........ 514/241 |
| 2002/0028811 A1 | 3/2002 | Heinemann et al. ........ 514/241 |

FOREIGN PATENT DOCUMENTS

| DE | 196 11 653 A1 * | 4/1997 |
|---|---|---|
| EP | 0 623 604 A2 | 11/1994 |
| GB | 2253624 | 9/1992 |
| WO | WO-95 17376 A1 * | 6/1995 |

OTHER PUBLICATIONS

Journal of Organic Chem. (month unavailable) 1994, pp. 203–213, Hiroi et al, The Palladium. Catalyzed Asymmetric a–allylations of Carbonyl Compounds with Chiral Allyl Esters via Enamines and Imines[1,2].

Journal of Hetro. Chem. vol. 30, Mar.–Apr. 1993, pp. 357–359, Unangst et al, Preparation of Novel 1,2,4–Thiadiazoles by Cyclization With 4–Mehtylbenzenesulfonyl Cyanide (Tosyl Cyanide) [1].

Journal of Chem. Soc., (month unavaliable) 1955, Chesterfield et al, Pyrimidines, Part VIII, Halogen–and Hydrazino–pyrimidines, pp. 3478–3480.

Chem. Ber. 97, (month unavailable) 1964, pp. 225–237, Goerdeler et al, präparative und kinetische Untersuchungen der nucleophilen Substitution von Halogenthiodiazolen.

* cited by examiner

Primary Examiner—Richard L. Raymond
Assistant Examiner—Venkataraman Balasubramanian

(57) ABSTRACT

The invention relates to novel fluoromethoximino compounds, to a process for their preparation and to their use as pesticides, and also to novel intermediates and to a plurality of processes for their preparation.

8 Claims, No Drawings

FLUOROMETHOXIMINO COMPOUNDS

This application is a divisional application of Ser. No. 09/445,084, filed Dec. 2, 1999 now U.S. Pat. No. 6,306,855, which is a 371 of PCT/EP98/03038, filed May 22, 1998.

The invention relates to novel fluoromethoximino compounds, to processes for their preparation and to their use as pesticides, and also to novel intermediates and to a plurality of processes for their preparation.

It is already known that certain fluoromethoximino compounds which are constitutionally similar to the compounds described below have fungicidal properties (compare, for example, WO 95/17 376 and DE-9 611 653). However, in many cases, the fungicidal activity of these compounds is unsatisfactory.

This invention, accordingly, provides the novel fluoromethoximino compounds of the general formula (I)

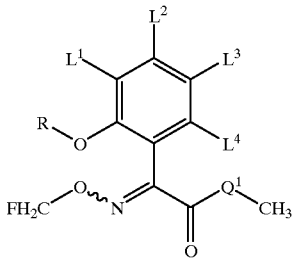
(I)

in which
$Q^1$ represents oxygen or —NH—,
R represents a grouping

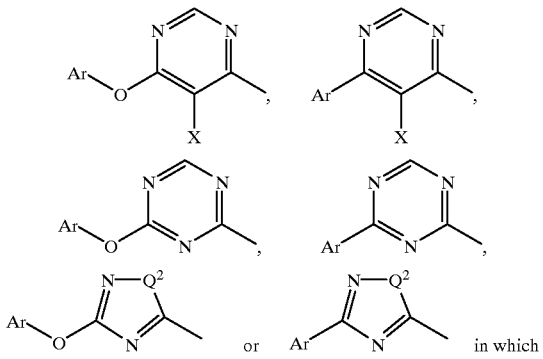

in which
Ar represents optionally substituted aryl,
$Q^2$ represents oxygen or sulphur,
X represents hydrogen or halogen and
$L^1$, $L^2$, $L^3$ and $L^4$ are identical or different and independently of one another each represents hydrogen, halogen, cyano, nitro, in each case optionally halogen-substituted alkyl, alkoxy, alkylthio, alkylsulphinyl or alkylsulphonyl.

Aryl preferably represents aromatic, mono- or polycyclic hydrocarbon rings, such as, in particular, phenyl, naphthyl, anthranyl, phenanthryl, preferably phenyl or naphthyl, especially phenyl.

Halogen preferably represents fluorine, chlorine, bromine or iodine, in particular fluorine, chlorine or bromine.

Furthermore, it has been found that the novel fluoromethoximino compounds of the general formula (I) are obtained when (process a) hydroxyaryl compounds of the general formula (II)

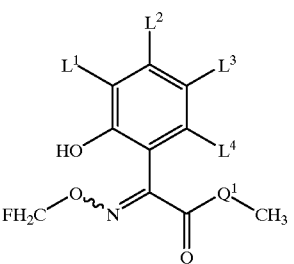
(II)

in which
$Q^1$, $L^1$, $L^2$, $L^3$ and $L^4$ are as defined above,
are reacted with a heterocyclyl derivative of the general formulae (III), (IV), (V), (VI), (VII) or (VIII)

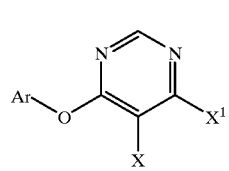
(III)

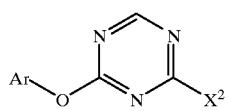
(IV)

(V)

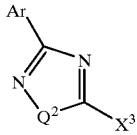
(VI)

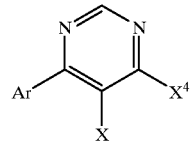
(VII)

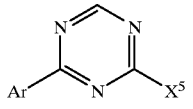
(VIII)

in which
Ar, $Q^2$ and X are as defined above and
$X^1$, $X^2$, $X^3$, $X^4$, $X^5$ and $X^6$ represent halogen, alkylsulphonyl or arylsulphonyl,
if appropriate in the presence of an acid acceptor and if appropriate in the presence of a diluent.

It is also possible to obtain fluoromethoximino compounds of the formula (I) where the meaning of $Q^1$ is NH (process a1) by reacting fluoromethoximino compounds of the formula (I) according to the invention where the meaning of $Q^1$ is oxygen with methylamine, if appropriate in the presence of a diluent, such as, for example, methanol, ethanol or tetrahydrofuran.

Finally, it has been found that the fluoromethoximino compounds of the formula (I) have very good microbicidal properties and can be used for protecting plants against harmful organisms.

Surprisingly, the substances according to the invention have better activity than constitutionally similar active compounds of the prior art with the same direction of action.

If appropriate, the compounds according to the invention can be present as mixtures of different possible isomeric forms, in particular stereoisomers, such as, for example, E and Z. What is claimed are both the E and the Z isomers, and also any mixtures of these isomers.

The invention preferably provides compounds of the formula (I) in which $Q^1$ represents oxygen or —NH—, R represents a grouping

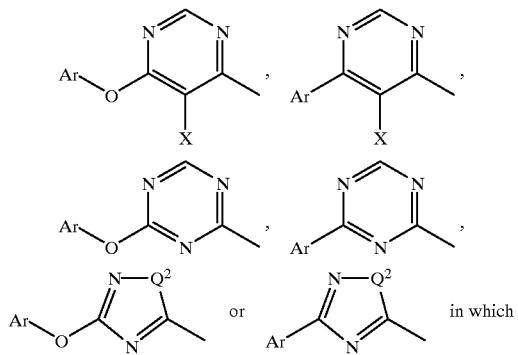

or in which

Ar represents optionally mono- to trisubstituted phenyl or optionally mono- to tetrasubstituted naphthyl, where the possible substituents are preferably selected from the list below:

halogen, cyano, nitro, amino, hydroxyl, mercapto, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, cycloalkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms, cycloalkyl, cycloalkenyl, cycloalkoxy or cycloalkenyloxy having in each case 3 to 7 carbon atoms and being in each case optionally substituted by 1 to 4 halogen atoms, and saturated heterocyclyl which is attached via nitrogen, $Q^2$ represents oxygen or sulphur, X represents hydrogen, fluorine, chlorine or bromine and $L^1$, $L^2$, $L^3$ and $L^4$ are identical or different and independently of one another each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms.

In the definitions, the saturated or unsaturated hydrocarbon chains, such as alkyl, alkenyl or alkinyl, are in each case straight-chain or branched, including in combination with heteroatoms, such as in alkoxy, alkylthio or alkylamino.

Cycloalkyl represents saturated, carbocyclic cyclic compounds which, if appropriate, form a polycyclic ring system with other carbocyclic, fused-on or bridged rings.

The invention relates in particular to compounds of the formula (I) in which $Q^1$ represents oxygen or —NH—, R represents a grouping

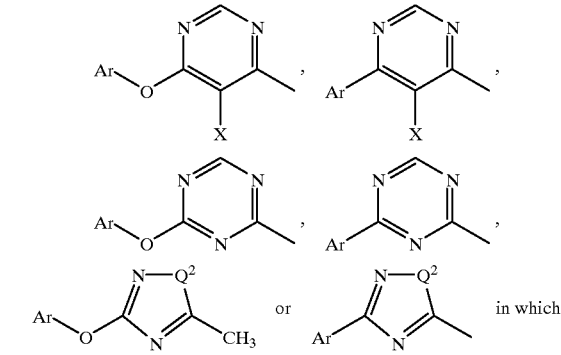

or in which

Ar represents phenyl which is optionally mono- or disubstituted by identical or different substituents, where the possible substituents are preferably selected from the list below:

fluorine, chlorine, bromine, cyano, nitro, methyl, ethyl, n- or i-propyl, n-, i-, s- or t-butyl, propenyl, but-3-en-2-yl, 2-methylpropenyl, cyclopropyl, methoxy, ethoxy, n- or i-propoxy, allyloxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached propylene, butylene or pentylene or in each case doubly attached methylenedioxy or ethylenedioxy, each of which is optionally mono- to tetrasubstituted by identical or different substituents from the group consisting of fluorine, chlorine, methyl, trifluoromethyl and ethyl, $Q^2$ represents oxygen or sulphur, X represents hydrogen, fluorine or chlorine and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

Very particular preference is given to compounds of the general formula (I) in which $Q^1$ represents oxygen or —NH—, R represents a grouping

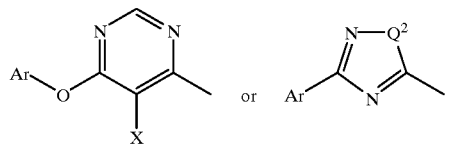

in which

Ar represents phenyl which is optionally mono- or disubstituted by identical or different substituents, where the possible substituents are preferably selected from the list below:

fluorine, chlorine, bromine, cyano, nitro, methyl, ethyl, n- or i-propyl, n-, i-, s- or t-butyl, but-3-en-2-yl, 2-methylpropenyl, cyclopropyl, methoxy, ethoxy, n- or i-propoxy, allyloxy, methylthio, ethylthio, n- or i-propylthio, trifluoromethyl, trifluoroethyl, difluoromethoxy, trifluoromethoxy, trifluoroethoxy, difluoromethylthio, trifluoromethylthio, methoxycarbonyl, ethoxycarbonyl, methoximinomethyl, ethoximinomethyl, methoximinoethyl, ethoximinoethyl, in each case doubly attached propylene, butylene or pentylene or in each case doubly attached methylenedioxy or ethylenedioxy, each of which is optionally mono- to tetrasubstituted by identical or different substituents selected from the group consisting of fluorine, chlorine, methyl, trifluoromethyl and ethyl, $Q^2$ represents oxygen or sulphur, X represents hydrogen, fluorine or chlorine and $L^1$ and $L^3$ are identical or different and independently of one another each represents hydrogen or methyl and $L^2$ and $L^4$ represent hydrogen.

In the general formula (I)

$Q^1$ preferably represents oxygen and in particular represents —NH—.

In the general formula (I)

R also preferably represents a grouping

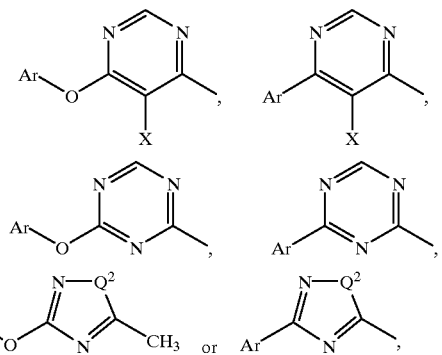

and in particular represents a grouping

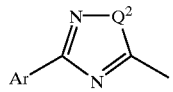

and very particularly preferably represents

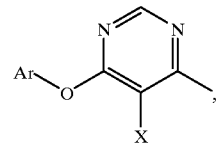

in which in each case $Q^2$ preferably represents oxygen and in particular represents sulphur, X preferably represents hydrogen or halogen and in particular represents fluorine and Ar preferably represents unsubstituted or mono- to trisubstituted phenyl or unsubstituted or mono- to tetrasubstituted naphthyl, and in particular represents mono- or disubstituted phenyl.

The substituents of Ar are preferably selected from the list below:

halogen, cyano, nitro, amino, hydroxyl, mercapto, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, cycloalkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, in each case doubly attached alkylene or dioxyalkylene having in each case 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms, cycloalkyl, cycloalkenyl, cycloalkoxy or cycloalkenyloxy having in each case 3 to 7 carbon atoms and being in each case optionally substituted by 1 to 4 halogen atoms, and saturated heterocyclyl which is attached via nitrogen.

The substituents of Ar are in particular selected from the list below:

fluorine, chlorine, bromine, cyano, nitro, methyl, ethyl, n- or i-propyl, n-, i-, s- or t-butyl, propenyl, but-3-en-2-yl, 2-methylpropenyl, cyclopropyl, methoxy, ethoxy, n- or i-propoxy, allyloxy, methylthio, ethylthio, n- or i-propylthio, methylsulphinyl, ethylsulphinyl, methylsulphonyl or ethylsulphinyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, in each case doubly attached propylene, butylene or pentylene or in each case doubly attached methylenedioxy or ethylenedioxy, each of which is optionally mono- to tetrasubstituted by identical or different substituents from the group consisting of fluorine, chlorine, methyl, trifluoromethyl and ethyl.

The substituents of Ar are particularly preferably selected from the list below:

fluorine, chlorine, bromine, cyano, nitro, methyl, ethyl, n- or i-propyl, n-, i-, s- or t-butyl, but-3-en-2-yl, 2-methylpropenyl, cyclopropyl, methoxy, ethoxy, n- or i-propoxy, allyloxy, methylthio, ethylthio, n- or i-propylthio, trifluoromethyl, trifluoroethyl, difluoromethoxy, trifluoromethoxy, trifluoroethoxy, difluoromethylthio, trifluoromethylthio, methoxycarbonyl, ethoxycarbonyl, methoximinomethyl, ethoximinomethyl, methoximinoethyl, ethoximinoethyl, in each case doubly attached propylene, butylene or pentylene or in each case doubly attached methylenedioxy or ethylenedioxy, each of which is optionally mono- to tetrasubstituted by identical or different substituents selected from the group consisting of fluorine, chlorine, methyl, trifluoromethyl and ethyl.

In the general formula (I)

$L^1$ and $L^3$ are identical or different and independently of one another each preferably represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms and in particular represents hydrogen.

In the general formula (I)

$L^2$ and $L^4$ are identical or different and independently of one another each preferably represents hydrogen, halogen, cyano, nitro, represents alkyl such as, in particular, methyl, alkoxy, alkylthio, alkylsulphinyl or alkylsulphonyl having in each case 1 to 6 carbon atoms and being in each case optionally substituted by 1 to 5 halogen atoms and in particular represents hydrogen.

The abovementioned general or preferred radical definitions apply both to the end products of the formula (I) and, correspondingly, to the starting materials or intermediates required in each case for the preparation.

The radical definitions given in the respective combinations or preferred combinations of radicals specifically for these radicals are, independently of the combination given in each case, also replaced by radical definitions of other preferred ranges.

The formula (II) provides a general definition of the hydroxyaryl compounds required as starting materials for carrying out the process a) according to the invention. In this formula (II), $Q^1$, $L^1$, $L^2$, $L^3$ and $L^4$ preferably or in particular have those meanings which have already been mentioned in connection with the description of the compounds of the formula (I) according to the invention as being preferred or as being particularly preferred for $Q^1$, $L^1$, $L^2$, $L^3$ and $L^4$.

The hydroxyaryl compounds of the formula (II) have not yet been disclosed; as novel substances, they form part of the subject matter of the present application.

The hydroxyaryl compounds of the formula (II) are obtained (process b) by hydrolysing acetals of the formula (IX)

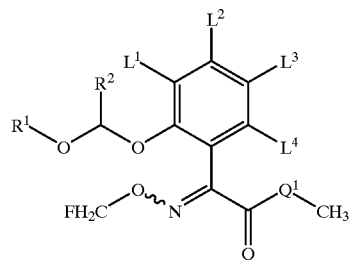

(IX)

in which $R^1$ represents alkyl, $R^2$ represents hydrogen or alkyl or $R^1$ and $R^2$ together with the atoms to which they are attached represent a five- or six-membered heterocyclic ring and $Q^1$, $L^1$, $L^2$, $L^3$ and $L^4$ are as defined above, if appropriate in the presence of a diluent, preferably an aliphatic, alicyclic or aromatic hydrocarbon, such as, for example, petroleum ether, hexane, heptane, cyclohexane, methylcyclohexane, benzene, toluene, xylene or decalin; a halogenated hydrocarbon, such as, for example, chlorobenzene, dichlorobenzene, dichloromethane, chloroform, tetrachloromethane, dichloroethane or trichloroethane;

an ether, such as diethyl ether, diisopropyl ether, dioxane, tetrahydrofuran, 1,2-dimethoxyethane, 1,2-diethoxyethane or anisole; a nitrile, such as acetonitrile, propionitrile, n- or i-butyronitrile or benzonitrile; an ester such as methyl acetate or ethyl acetate; a sulphone, such as sulpholane; an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water and if appropriate in the presence of an acid, preferably an inorganic or organic protic or Lewis acid, such as, for example, hydrogen chloride, hydrogen bromide, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, aluminium tribromide, zinc chloride, iron(III) chloride, antimony pentachloride, or else a polymeric acid, such as, for example, an acid ion exchanger, an acidic alumina or acidic silica, at temperatures from −20° C. to 120° C., preferably at temperatures from −10° C. to 80° C.

Hydroxyaryl compounds of the formula (II) where the meaning of $Q^1$ is NH can also be obtained (process b1) by reacting hydroxyaryl compounds of the formula (II) where the meaning of $Q^1$ is oxygen with methylamine, if appropriate in the presence of a diluent, such as, for example, methanol, ethanol or tetrahydrofuran.

The formula (IX) provides a general definition of the acetals required as starting materials for carrying out the process b) according to the invention. In this formula (IX), $Q^1$, $L^1$, $L^2$, $L^3$ and $L^4$ preferably or in particular have those meanings which have already been mentioned in connection with the description of the compounds of the formula (I) according to the invention as being preferred or as being particularly preferred for $Q^1$, $L^1$, $L^2$, $L^3$ and $L^4$. $R^1$ represents alkyl, preferably represents methyl or ethyl, $R^2$ represents hydrogen or alkyl, preferably represents methyl or ethyl, or $R^1$ and $R^2$ together with the atoms to which they are attached represent a five- or six-membered heterocyclic ring, preferably represent tetrahydrofuryl or tetrahydropyryl.

The acetals of the formula (IX) have not yet been disclosed; as novel substances, they form part of the subject matter of the present application.

The acetals of the formula (IX) are obtained by (process c) reacting arylacetic acid derivatives of the formula (X)

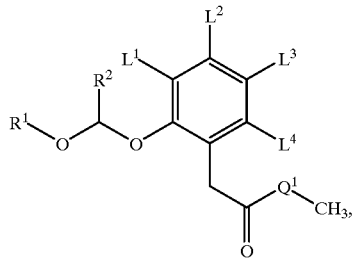

(X)

in which $R^1$, $R^2$, $Q^1$, $L^1$, $L^2$, $L^3$ and $L^4$ are as defined above, initially with a nitrosating agent, preferably with an alkali metal nitrite, such as, for example, sodium nitrite, or, in particular, with nitrosyl chloride or an alkyl nitrite, such as, for example, t-butyl nitrite or t-amyl nitrite, if appropriate in the presence of a diluent, preferably an ester, such as, for example, methyl acetate or ethyl acetate, or an alcohol, such as, for example, methanol or ethanol, and if appropriate in the presence of an acid acceptor, preferably an alkali metal hdroxide, carbonate or alkoxide, such as, for example, sodium methoxide or sodium ethoxide, at temperatures from −50° C. to 100° C., preferably from −20° C. to 50° C., and reacting the resulting oximes of the formula (XI)

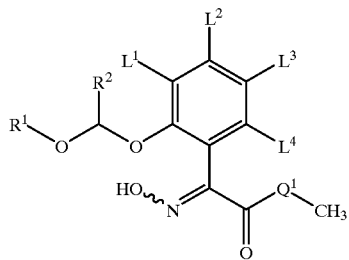

(XI)

in which $R^1$, $R^2$, $Q^1$, $L^1$, $L^2$, $L^3$ and $L^4$ are as defined above, preferably without further work-up with fluorobromomethane or fluorochloromethane, if appropriate in the presence of a diluent, preferably an aliphatic, alicyclic or aromatic hydrocarbon, such as, for example, petroleum ether, hexane, heptane, cyclohexane, methylcyclohexane, benzene, toluene, xylene or decalin; a halogenated hydrocarbon, such as, for example, chlorobenzene, dichlorobenzene, dichloromethane, chloroform, carbon tetrachloride, dichloroethane or trichloroethane; an ether, such as diethyl ether, diisopropylether, methyl t-butyl ether, methyl t-amyl ether, dioxane, tetrahydrofuran, 1,2-dimethoxyethane, 1,2-diethoxyethane or anisole; a ketone, such as acetone, butanone, methyl isobutyl ketone or cyclohexanone; a nitrile, such as acetonitrile, propionitrile, n- or i-butyronitrile or benzonitrile; an ester such as methyl acetate or ethyl acetate; an amide, such as N,N-dimethylformamide, N,N-dimethylacetamide, N-methylformanilide, N-methylpyrrolidone or hexamethylphosphoric triamide; a sulphoxide, such as dimethyl sulphoxide; a sulphone, such as sulpholane; an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water, and if appropriate in the presence of a base, preferably an alkaline earth metal hydride, hydroxide, amide, alkoxide, acetate, carbonate or bicarbonate or an alkali metal hydride, hydroxide, amide, alkoxide, acetate, carbonate or bicarbonate, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine, such as trimethylamine, triethylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), and if appropriate in the presence of a catalyst, preferably a Lewis acid, such as, for example, iron(III) chloride, aluminium chloride or aluminium bromide, at temperatures from −20° C. to 120° C., preferably at temperatures from −10° C. to 80° C.

Acetals of the formula (IX) where the meaning of $Q^1$ is NH can also be obtained (process c1) by reacting acetals of the formula (IX) where the meaning of $Q^1$ is oxygen with methylamine, if appropriate in the presence of a diluent, such as, for example, methanol, ethanol or tetrahydrofuran.

The formula (X) provides a general definition of the arylacetic acid derivatives required as starting materials for carrying out the process c) according to the invention for preparing the acetals of the formula (IX). In this formula (X), $Q^1$, $L^1$, $L^2$, $L^3$ and $L^4$ preferably or in particular have those meanings which have already been mentioned in connection with the description of the compounds of the formula (I) according to the invention as being preferred or as being particularly preferred for $Q^1$, $L^1$, $L^2$, $L^3$ and $L^4$. $R^1$ and $R^2$ preferably have those meanings which have already been mentioned in connection with the description of the compounds of the formula (IX) as being preferred.

The arylacetic acid derivatives of the formula (X) are known and/or can be prepared by known processes (compare, for example, J. Org. Chem. 1994, 203–13, and DE-9 611 653).

The formulae (III), (IV), (V), (VI), (VII) and (VIII) provide general definitions of the heterocyclyl derivatives furthermore required as starting materials for carrying out the process a) according to the invention. In these formulae (III), (IV), (V), (VI), (VII) and (VIII), Ar, $Q^2$ and X preferably or in particular have those meanings which have already been mentioned in connection with the description of the compounds of the formula (I) according to the invention as being preferred or as being particularly preferred for Ar, $Q^2$ and X. $X^1$, $X^2$, $X^3$, $X^4$, $X^5$ and $X^6$ independently of one another represent halogen, preferably represent fluorine or chlorine, or represent alkylsulphonyl or arylsulphonyl, preferably represent methylsulphonyl, benzylsulphonyl or tolylsulphonyl.

The heterocyclyl derivatives of the formulae (III), (IV), (V), (VI), (VII) and (VIII) are known chemicals for synthesis and/or can be prepared by known processes (compare, for example, J. Heterocyclic Chem. 30, 357 (1993), J. Chem. Soc., 1955; 3478, 3480, Chem. Ber., 97, 225–237, (1964), DE-9 611 653).

Suitable diluents for carrying out the processes a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropylether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The process a) according to the invention is, if appropriate, carried out in the presence of a suitable acid acceptor. Suitable acid acceptors are all customary inorganic or organic bases. These preferably include alkaline earth metal hydrides, hydroxides, amides, alkoxides, acetates, carbonates or bicarbonates or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process a) according to the invention, the reaction temperatures can be varied within a relatively wide range. In general, the process is carried out at temperatures from 0° C. to 150° C., preferably at temperatures from 0° C. to 80° C.

For carrying out the process a) according to the invention for preparing the compounds of the formula (I), generally 0.2 to 5 mol, preferably 0.5 to 2 mol, of a heterocyclyl derivative of the formulae (III), (IV), (V), (VI), (VII) or (VIII) are employed per mole of the hydroxyaryl compounds of the general formula (II).

All processes according to the invention are generally carried out under atmospheric pressure. However, it is also possible to operate under elevated or reduced pressure—in general between 0.1 bar and 10 bar.

The practice of the reaction and the work-up and isolation of the reaction products is carried out by known processes (cf. also the Preparation Examples).

The substances according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochlilobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well-tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Puccinia species, and for controlling diseases in viticulture and fruit and vegetable growing, such as, for example, against Venturia and Plasmopara species. Furthermore, the active compounds according to the invention are also suitable for increasing the yield of crops. Moreover, they have low toxicity and are well-tolerated by plants.

In the protection of materials, the substances according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis,*

Aspergillus, such as *Aspergillus niger,*

Chaetomium, such as *Chaetomium globosum,*

Coniophora, such as *Coniophora puetana,*

Lentinus, such as *Lentinus tigrinus,*

Penicillium, such as *Penicillium glaucum,*

Polyporus, such as *Polyporus versicolor,*

Aureobasidium, such as *Aureobasidium pullulans,*

Sclerophoma, such as *Sclerophoma pityophila,*

Trichoderma, such as *Trichoderma viride,*

Escherichia, such as *Escherichia coli,*

Pseudomonas, such as *Pseudomonas aeruginosa,*

Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is, emulsifiers and/or dispersants, and/or foam-formers. If the extender used is water, it is also possible to employ for example organic solvents as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite, dolomite, or else synthetic granules of inorganic and organic meals, and granules of organic material such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol, polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide, Prussian Blue and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the efficacy of the mixture exceeds the efficacy of the individual components.

Examples of co-components in mixtures are the following compounds:
Fungicides:
aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovalediode, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-b-propyl-1H-1,2,4-triazole-1-ethanol,
α-(2,4-dichlorophenyl)-β-methoxy-a-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-a-(methoxyimino)-N-methyl-2-phenoxy-phenylacetamide,
1-isopropyl{2-methyl-1-[[[1-(4-methylphenyl)-ethyl]-amino]-carbonyl]-propyl}-carbamate,
1-(2,4-dichlorophenyl)-2-(1H-1,2,4-triazol-1-yl) ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin,

*Bacillus thuringiensis*, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboximn, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethlrin, triarathen, triazophos, triazuron, trichlorfon, triflumuron, trimethacarb, vamidothion, XMC, xylylcarb, zetamethrin.

It is also possible to admix other known active compounds, such as herbicides or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

Using the active compounds according to the invention as fungicides, the application rates can be varied within a relatively wide range, depending on the type of application. In the treatment of parts of plants, the active compound application rates are generally between 0.1 and 10,000 g/ha, preferably between 10 and 1000 g/ha. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/ha.

The compositions employed for protecting industrial materials generally comprise the active compounds in an amount of from 1 to 95%, preferably from 10 to 75%.

The use concentrations of the active compounds according to the invention depend on the species and the occurrence of the microorganisms to be controlled and on the composition of the material to be protected. The optimum rate of application can be determined by test series. In general, the use concentrations are in the range from 0.001 to 5% by weight, preferably from 0.05 to 1.0% by weight, based on the material to be protected.

The efficacy and the activity spectrum of the active compounds to be used according to the invention in the protection of materials, and/or of the compositions, concentrates or quite generally formulations preparable therefrom can be increased by adding, if appropriate, further antimicrobially active compounds, fungicides, bactericides, herbicides, insecticides or other active compounds for broadening the activity spectrum or to obtain particular effects, such as, for example, additional protection against insects. These mixtures may have a broader activity spectrum than the compounds according to the invention.

PREPARATION EXAMPLES

Example 1

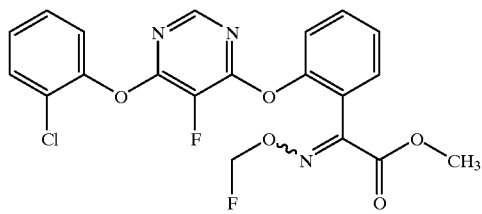

Process a)

A mixture of 0.6 g (0.003 mol) of methyl 2-fluoromethoxyimino-2-(2-hydroxyphenyl)-acetate, 0.6 g (0.003 mol) of 4-(2-chlorophenoxy-5,6-difluoropyrimidine and 0.4 g of potassium carbonate in 20 ml of acetonitrile is stirred at 50° C. overnight. After cooling, the mixture is concentrated under reduced pressure, and the residue is taken up in ethyl acetate, washed with water, dried over sodium sulphate and once more concentrated under reduced pressure. The residue is chromatographed over silica gel using hexane/acetone (4:1). This gives 0.3 g (22% of theory) of methyl {2-[6-(2-chlorophenoxy)-5-fluoropyrimidin-4-yloxy]-phenyl}-fluoromethoxyimino-acetate of melting point 153–155° C.

Example 2

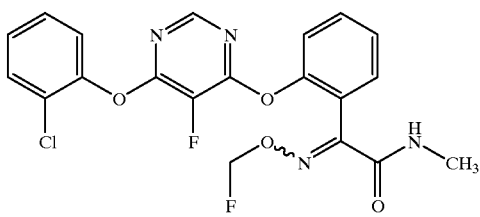

Process a)

A mixture of 25 g (0.111 mol) of 2-fluoromethoxyimino-2-(2-hydroxyphenyl)-N-methylacetamide, 26.8 g (0.111 mol) of 4-(2-chlorophenoxy-5,6-difluoropyrimidine and 18.3 g of potassium carbonate in 300 ml of acetonitrile is stirred at 50° C. overnight. After cooling, the mixture is poured into ice water and extracted twice with dichloromethane. The combined organic phases are dried over sodium sulphate and concentrated under reduced pressure. The residue is chromatographed over silica gel using hexane/acetone (7:3). This gives 27.3 g (55% of theory) of 2-{2-[6-(2-chlorophenoxy)-5-fluoropyrimidin-4-yloxy]-phenyl}-2-fluoromethoxyimino-N-methylacetamide of melting point 128–129° C.

Example 3

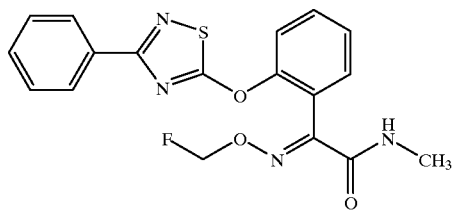

Process a)

0.1 g of an 80% strength suspension of sodium hydride is added to a solution of 0.7 g of 2-fluoromethoxyimino-2-(2-hydroxyphenyl)-N-methylacetamide and 5-phenylsulphonyl-3-phenyl-<1,2,4>thiadiazole in 20 ml of N-methylpyrrolidone, and the mixture is stirred at room temperature overnight. The reaction mixture is then concentrated under reduced pressure, and the residue is taken up in ethyl acetate, washed twice with water, dried over sodium sulphate and once more concentrated under reduced pressure. The residue is chromatographed over silica gel using hexane/acetone (4:1). This gives 0.6 g (50% of theory) of 2-fluoromethoxyimino-N-methyl-2-[2-(3-phenyl-[1,2,4]thiadiazol-5-yloxy)-phenyl]-acetamide.

logP value: 2.9

Preparation of the Starting Materials of the Formula (II)

Example (II-1)

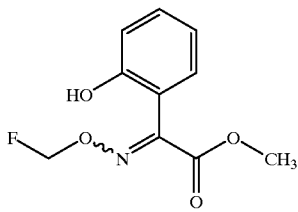

Process b)

A solution of 3.1 g (0.01 mol) of methyl 2-fluoromethoxyimino-2-[2-(tetrahydropyran-2-yloxy)-phenyl]-acetate in 30 ml of ethyl acetate is treated with 0.2 g of acidic ion exchange resin and stirred at 20° C. overnight (approximately 16 hours). The ion exchange resin is then filtered off and the filtrate is concentrated under reduced presssure. The residue is chromatographed over silica gel using hexane/acetone (9:1). This gives 0.7 g (31% of theory) of methyl 2-fluoromethoxyimino-2-(2-hydroxyphenyl)-acetate.

logP value: 1.6

Example (II-2)

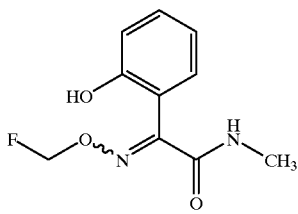

Process b1)

A solution of 3.1 g (0.01 mol) of 2-fluoromethoxyimino-N-methyl-2-[2-(tetrahydropyran-2-yloxy)-phenyl]-acetamide in 30 ml of methanol is treated with 0.1 g of acidic ion exchange resin and stirred at 20° C. overnight (approximately 16 hours). The ion exchange resin is then filtered off and the filtrate is concentrated under reduced presssure. The residue is chromatographed over silica gel using hexane/acetone (9:1). This gives 0.9 g (40% of theory) of 2-fluoromethoxyimino-2-(2-hydroxyphenyl)-N-methylacetamide.

logP value: 1.1

Preparation of Intermediates of the Formula (IX)

Example (VI-1)

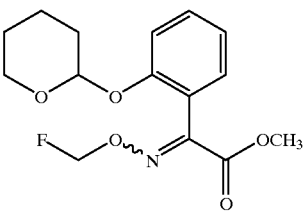

Process c)

Over a period of 30 minutes, a solution of 75 g (0.3 mol) of methyl [2-(tetrahydropyran-2-yloxy)-phenyl]-acetate and 102.9 g (0.9 mol) of 90% strength t-butyl nitrite is added dropwise to a solution of 39.6 g (0.33 mol) of potassium tert-butoxide in 360 ml of t-butanol, the temperature of the reaction mixture rising to 45° C. The mixture is stirred at room temperature for 2 hours and then cooled to 15° C., and 51 g (0.45 mol) of bromofluoromethane are added dropwise over a period of from 5 to 10 minutes. The mixture is stirred overnight without any further cooling and then taken up in methyl t-butyl ether, washed with water, dried over sodium sulphate and concentrated under reduced pressure. The residue is chromatographed over silica gel using hexane/acetone (9:1). This gives 42.8 g (45.9% of theory) of methyl 2-fluoromethoxyimino-2-[2-(tetrahydropyran-2-yloxy)-phenyl]-acetate as an oil.

logP value: 2.8

Example (VI-2)

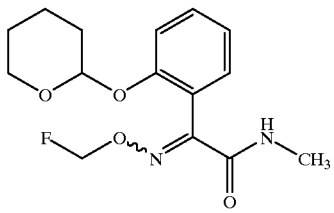

Process c1)

With cooling, methylamine is introduced over a period of 15 minutes into a solution of 6.2 g (0.02 mol) of methyl 2-fluoromethoxyimino-2-[2-(tetrahydropyran-2-yloxy)-phenyl]-acetate in 50 ml of methanol. The temperature of the solution should not exceed 40° C. Stirring is continued overnight, and the mixture is then concentrated under reduced pressure. The residue is chromatographed over silica gel using hexane/acetone (7:3). This gives 5.5 g (88.7% of theory) of 2-fluoromethoxyimino-N-methyl-2-[2-(tetrahydropyran-2-yloxy)-phenyl]-acetamide of melting point 81° C.

Preparation of Starting Materials of the Formula (III)

Example (III-1)

At 0° C., a solution of 42.4 g (0.45 mol) of phenol and 50.4 g (0.45 mol) of potassium tert-butoxide in 400 l of tetrahydrofuran is added dropwise to a solution of 80 g (0.6 mol) of 4,5,6-trifluoropyrimidine irr 1 l of tetrahydrofuran. After the addition has ended, the reaction mixture is stirred at 0° C. for 30 minutes and then poured into water and extracted with ethyl acetate. The organic phase is dried over sodium sulphate, concentrated under reduced pressure, and the residue is stirred with low-boiling petroleum ether. This gives 63.8 g (68.1% of theory) of 4-phenoxy-5,6-difluoropyrimidine of melting point 65 to 66° C.

Preparation of the Precursor

To dry a mixture of 609 g of potassium fluoride in 2.3 l of sulpholane, 500 ml of liquid are distilled off at 145° C. and 20 mbar. 1054 g of 5-chloro-4,6-difluoropyrimidine (DE-A 3843558) and 25 g of tetraphenylphosphonium bromide are subsequently added, 5 bar of nitrogen are applied and the mixture is stirred at 240° C. for 24 hours, the pressure increasing to 11 bar. The reaction mixture is cooled to 80° C. and vented. The mixture is then slowly heated again at atmospheric pressure, and the product is distilled off. Once the bottom temperature has reached 200° C., the pressure is lowered to 150 mbar to accelerate the distillation and to obtain more product. Altogether, 664 g (70.7% of theory) of 4,5,6-trifluoropyrimidine of boiling point 86 to 87° C. are obtained.

The logP values are determined in accordance with EEC Directive 79/831 Annex V. A8 by HPLC (gradient method, acetonitrile/0.1% aqueous phosphoric acid).

The compounds of the formula (I-a) according to the invention listed in Table 1 below are likewise obtained by the methods of Examples (1) to (3), and in accordance with the general description of the preparation processes a) and a1) according to the invention:

TABLE 1

(I-a)

| Ex. No. | R | Q | phys. data |
|---|---|---|---|
| 4 | (5-fluoro-6-methylpyrimidin-4-yl), 3-chloro-2-methylphenyl | NH | logP value: 3.5 |
| 5 | (5-fluoro-6-methylpyrimidin-4-yl), 2,3-dichlorophenyl | NH | logP value: 3.4 |
| 6 | (5-fluoro-6-methylpyrimidin-4-yl), 2-(OCHF$_2$)phenyl | NH | logP value: 2.9 |
| 7 | (5-fluoro-6-methylpyrimidin-4-yl), phenyl | NH | logP value: 2.7 |
| 8 | (5-fluoro-6-methylpyrimidin-4-yl), 2-nitrophenyl | NH | logP value: 2.7 |

TABLE 1-continued (I-a)

| Ex. No. | R | Q | phys. data |
|---|---|---|---|
| 9 | 5-fluoro-6-methyl-pyrimidin-4-yl-oxy-(2,3-dimethylphenyl) | NH | logP value: 3.3 |
| 10 | 5-fluoro-6-methyl-pyrimidin-4-yl-oxy-(2-cyanophenyl) | NH | logP value: 2.8 |
| 11 | 5-fluoro-6-methyl-pyrimidin-4-yl-oxy-(2-methylphenyl) | NH | logP value: 3.0 |
| 12 | 5-fluoro-6-methyl-pyrimidin-4-yl-oxy-(2-methyl-3-chlorophenyl) | O | |
| 13 | 5-methyl-3-phenyl-1,2,4-thiadiazol-yl | O | logP value: 3.6 |
| 14 | 5-methyl-3-(4-fluorophenyl)-1,2,4-thiadiazol-yl | NH | |
| 15 | 5-methyl-3-(4-chlorophenyl)-1,2,4-thiadiazol-yl | NH | |
| 16 | 5-methyl-3-(4-bromophenyl)-1,2,4-thiadiazol-yl | NH | |
| 17 | 5-methyl-3-phenyl-1,2,4-oxadiazol-yl | NH | |

TABLE 1-continued

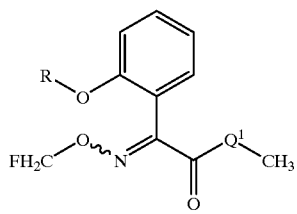
(I-a)

| Ex. No. | R | Q | phys. data |
|---|---|---|---|
| 18 | 5-methyl-3-(4-methylphenyl)-1,3,4-thiadiazol-2-yl | NH | |
| 19 | 5-methyl-3-(4-trifluoromethylphenyl)-1,3,4-thiadiazol-2-yl | NH | logP value: 3.7 |
| 20 | 5-methyl-3-(4-trifluoromethylphenyl)-1,3,4-thiadiazol-2-yl | O | |
| 21 | 5-methyl-3-(4-trifluoromethoxyphenyl)-1,3,4-thiadiazol-2-yl | O | |
| 22 | 5-methyl-3-(4-trifluoromethoxyphenyl)-1,3,4-thiadiazol-2-yl | NH | logP value: 3.8 |
| 23 | 5-methyl-3-(3-trifluoromethoxyphenyl)-1,3,4-thiadiazol-2-yl | NH | logP value: 3.8 |
| 24 | 5-methyl-3-(3-trifluoromethoxyphenyl)-1,3,4-thiadiazol-2-yl | O | |
| 25 | 5-methyl-3-(3-difluoromethoxyphenyl)-1,3,4-thiadiazol-2-yl | NH | logP value: 3.2 |
| 26 | 5-methyl-3-(4-difluoromethoxyphenyl)-1,3,4-thiadiazol-2-yl | NH | logP value: 3.2 |
| 27 | 5-fluoro-6-methyl-4-(2-chloro-3-methylphenoxy)pyrimidin-yl | NH | logP value: 3.32 |

TABLE 1-continued (I-a)

[Structure: methyl (E)-2-[2-(R-oxy)phenyl]-2-(fluoromethoxyimino)acetate with Q¹ = Q linkage]

| Ex. No. | R | Q | phys. data |
|---|---|---|---|
| 28 | 5-methyl-3-[3-(trifluoromethyl)phenyl]-1,3,4-thiadiazol-2-yl | NH | logP value: 3.6 |
| 29 | 6-methylpyrimidin-4-yl linked via O to 2-chlorophenyl | NH | logP value: 2.7 |

USE EXAMPLES

Example A
Plasmopara Test (Grapevine)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the substances according to the invention listed in Examples (1), (2), (3), (4), (6), (7), (8), (9), (10), (11), (19), (22), (23), (25), (26), (27), (28) and (29) exhibit, at an application rate of 100 g/ha, an efficacy of 98% or more.

TABLE A

Plasmopara test (grapevine)/protective

| Active compound | Active compound application rate in g/ha | Efficacy in % |
|---|---|---|
| according to the invention: [Structure (1): pyrimidine with 2-chlorophenoxy and fluorinated phenoxyiminoacetate substituents] | 100 | 98 |

TABLE A-continued
Plasmopara test (grapevine)/protective
| Active compound | Active compound application rate in g/ha | Efficacy in % |
|---|---|---|
| 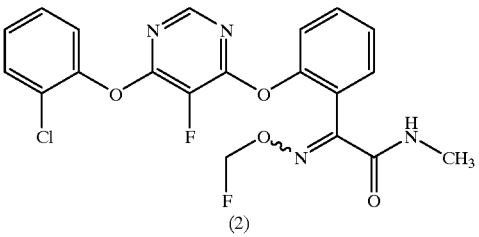 (2) | 100 | 100 |
according to the invention:
| | | |
|---|---|---|
| 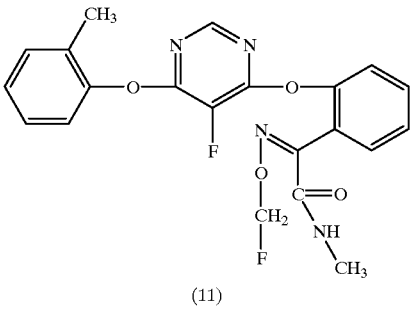 (11) | 100 | 100 |
| 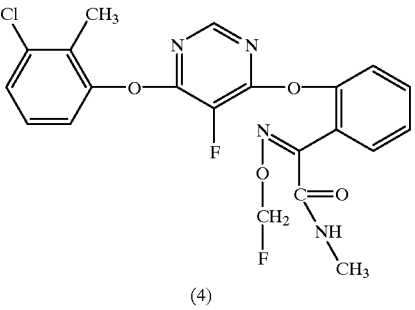 (4) | 100 | 100 |
| 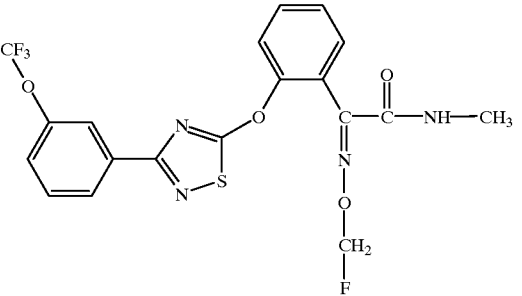 (23) | 100 | 100 |

TABLE A-continued

Plasmopara test (grapevine)/protective

| Active compound | Active compound application rate in g/ha | Efficacy in % |
|---|---|---|
| according to the invention: | | |
| (3) | 100 | 100 |
| (6) | 100 | 96 |
| (7) | 100 | 100 |

TABLE A-continued
Plasmopara test (grapevine)/protective
| Active compound | Active compound application rate in g/ha | Efficacy in % |
|---|---|---|
| according to the invention: | | |
| 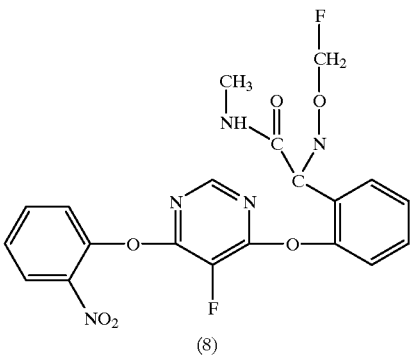 (8) | 100 | 96 |
| 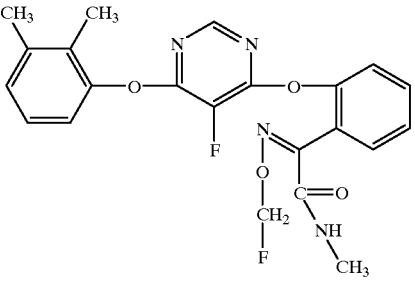 (9) | 100 | 100 |
| 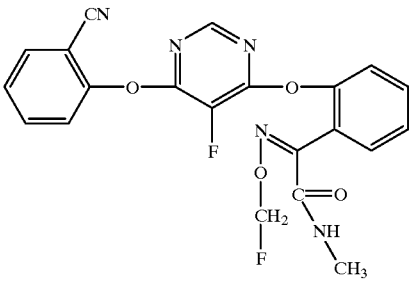 (10) | 100 | 96 |
| according to the invention: | | |
| 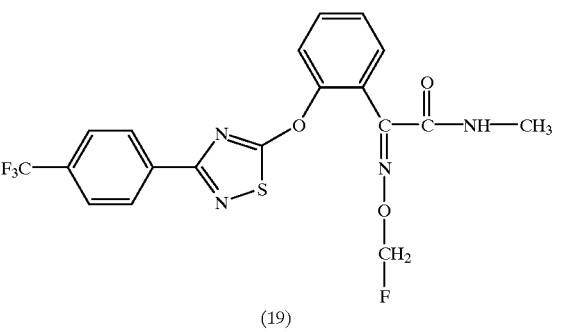 (19) | 100 | 100 |

TABLE A-continued
Plasmopara test (grapevine)/protective
| Active compound | Active compound application rate in g/ha | Efficacy in % |
|---|---|---|
| 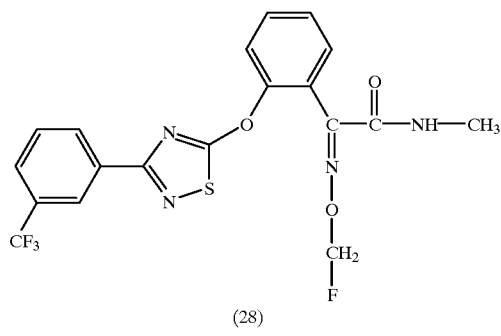 (28) | 100 | 100 |
| 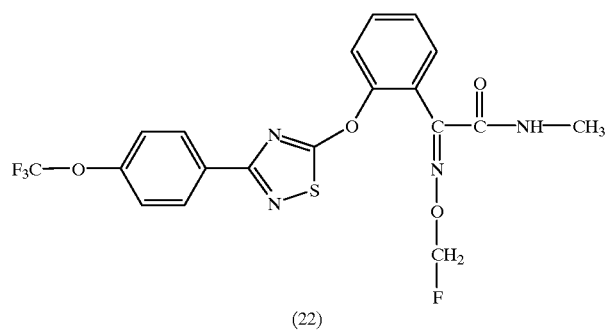 (22) | 100 | 100 |
according to the invention:
| | | |
|---|---|---|
| 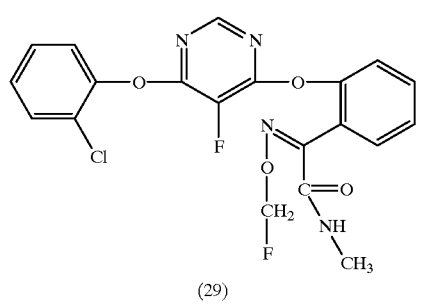 (29) | 100 | 100 |

TABLE A-continued

Plasmopara test (grapevine)/protective

| Active compound | Active compound application rate in g/ha | Efficacy in % |
|---|---|---|
| 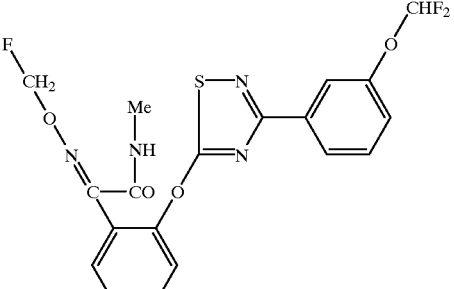<br>(25) | 100 | 99 |
| 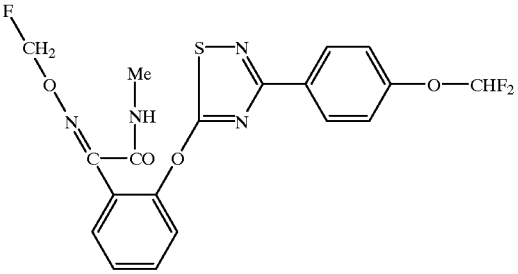<br>(26) | 100 | 100 | according to the invention:

| | | |
|---|---|---|
| 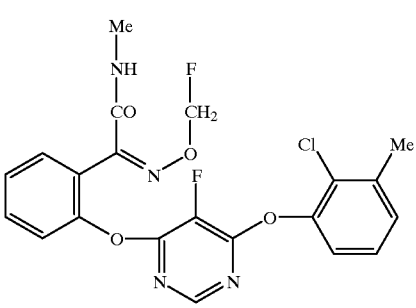<br>(27) | 100 | 100 |

Example B
Venturia Test (Apple)/Protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, the substances according to the invention listed in Examples (1), (2), (3), (4), (5), (6), (7), (9), (11), (19), (22), (23), (25), (26), (28) and (29) exhibit, at an application rate of 10 g/ha, an efficacy of 99% or more.

TABLE B
Venturia test (apple)/protective
| Active compound | Active compound application rate in g/ha | Efficacy in % |
|---|---|---|
| according to the invention: | | |
| 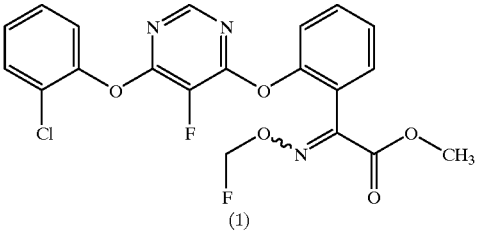 (1) | 10 | 100 |
| 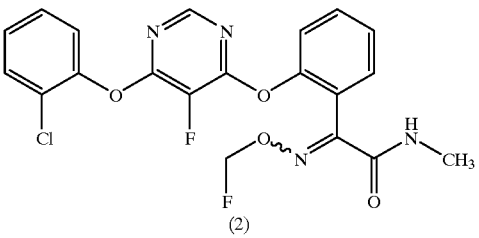 (2) | 10 | 99 |
| erfindungsgemäβ | | |
| 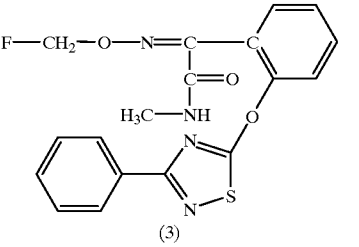 (3) | 10 | 100 |
| 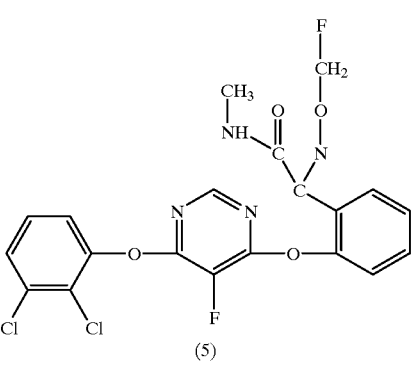 (5) | 10 | 96 |

TABLE B-continued

Venturia test (apple)/protective

| Active compound | Active compound application rate in g/ha | Efficacy in % |
|---|---|---|
| (6) | 10 | 95 | according to the invention:

| | | |
|---|---|---|
| (7) | 10 | 96 |
| (9) | 10 | 100 |
| (11) | 10 | 100 |

TABLE B-continued

Venturia test (apple)/protective

| Active compound | Active compound application rate in g/ha | Efficacy in % |
|---|---|---|
| according to the invention: | | |
| (4) | 10 | 98 |
| (23) | 10 | 100 |
| (19) | 19 | 100 |
| according to the invention: | | |
| (28) | 10 | 100 |

TABLE B-continued
Venturia test (apple)/protective
| Active compound | Active compound application rate in g/ha | Efficacy in % |
|---|---|---|
| 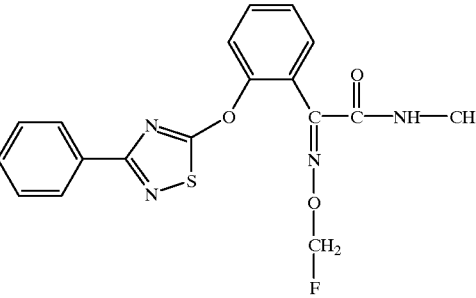 (22) | 10 | 100 |
| 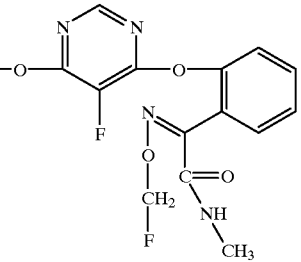 (29) | 10 | 100 |
| according to the invention: | | |
| 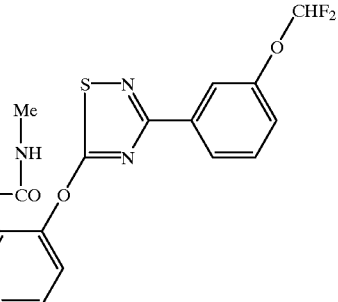 (25) | 10 | 100 |
| 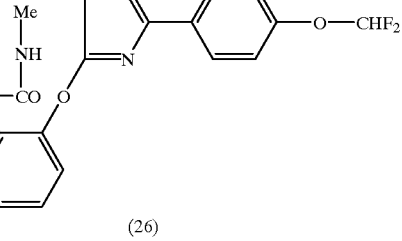 (26) | 10 | 99 |

Example C
Puccinia Test (Wheat)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of approximately 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

In this test, the substances according to the invention listed in Examples (1), (2), (5), (6), (7), (8), (9), (10), (11), (19), (28),22), (29) and (26) exhibit, at an application rate of 250 g/ha, an efficacy of 80% or more.

TABLE C

Puccinia test (wheat)/protective

| Active compound | Active compound application rate in g/ha | Efficacy in % |
|---|---|---|
| according to the invention: | | |
| (1) | 250 | 80 |
| (2) | 250 | 100 |
| according to the invention: | | |
| (5) | 250 | 100 |

TABLE C-continued

Puccinia test (wheat)/protective

| Active compound | Active compound application rate in g/ha | Efficacy in % |
|---|---|---|
| (6) | 250 | 100 |
| (7) | 250 | 100 |
| (8) | 250 | 100 |
| (9) | 250 | 100 |

TABLE C-continued
Puccinia test (wheat)/protective
| Active compound | Active compound application rate in g/ha | Efficacy in % |
|---|---|---|
| 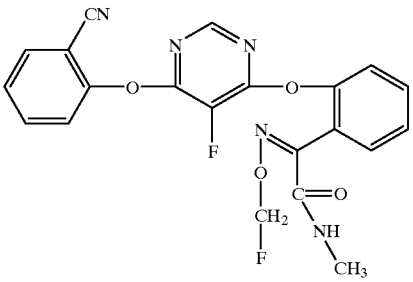 (10) | 250 | 100 |
| 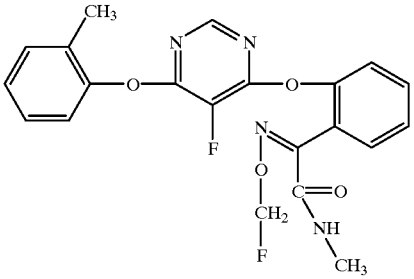 (11) | 250 | 100 |
| 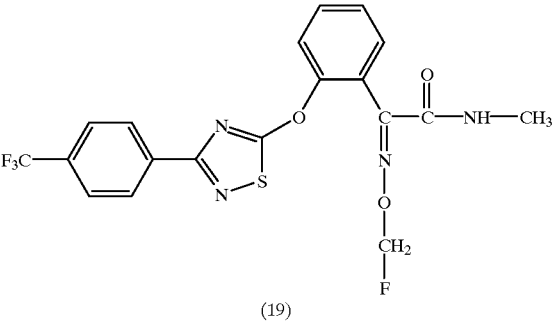 (19) | 250 | 100 |
| 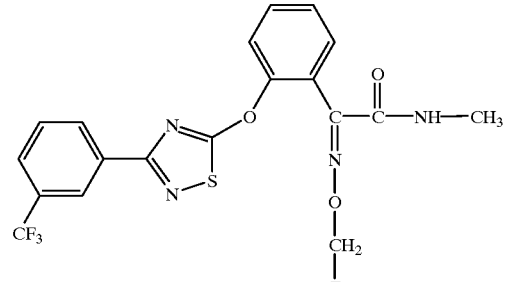 (28) | 250 | 100 |

TABLE C-continued

Puccinia test (wheat)/protective

| Active compound | Active compound application rate in g/ha | Efficacy in % |
|---|---|---|
| 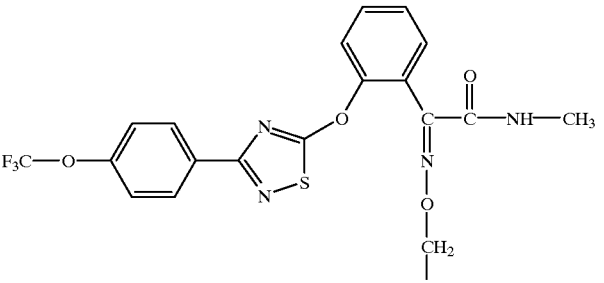 (22) | 250 | 100 |
| 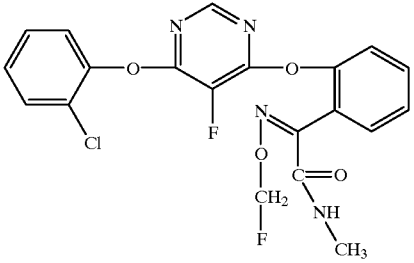 (29) | 250 | 100 |
| 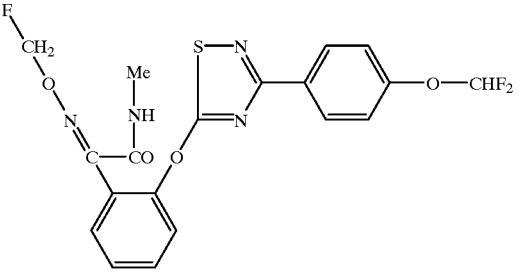 (26) | 250 | 100 |

Example D
Puccinia Test (Wheat)/Curative

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Puccinia recondite*. The plants remain in an incubation cabin at 20° C. and 100% relative atmospheric humidity for 48 hours. The plants are subsequently sprayed with the preparation of active compound at the stated application rate.

The plants are placed in a greenhouse at a temperature of approximately 20° C. and a relative atmospheric humidity of approximately 80% to promote the development of rust pustules.

Evaluation is carried out 10 days after the inoculation. 0% means an efficacy which corresponds to that of the control, whereas an efficacy of 100% means that no infection is observed.

In this test, the substance according to the invention listed in Examples (2), (4), (6), (8), (10), (28), (22) and (29) exhibits, at an application rate of 250 g/ha, an efficacy of 100%.

TABLE D

Puccinia test (wheat)/curative

| Active compound | Active compound application rate in g/ha | Efficacy in % |
|---|---|---|
| according to the invention: (2) | 250 | 100 |
| according to the invention: (4) | 250 | 100 |
| (6) | 250 | 100 |
| (8) | 250 | 100 |

TABLE D-continued
Puccinia test (wheat)/curative
| Active compound | Active compound application rate in g/ha | Efficacy in % |
|---|---|---|
| 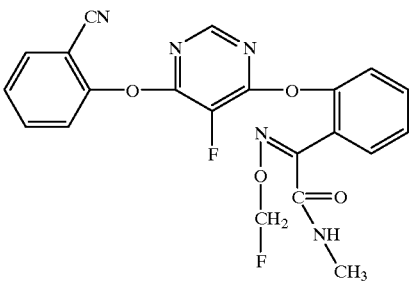<br>(10) | 250 | 100 |
| 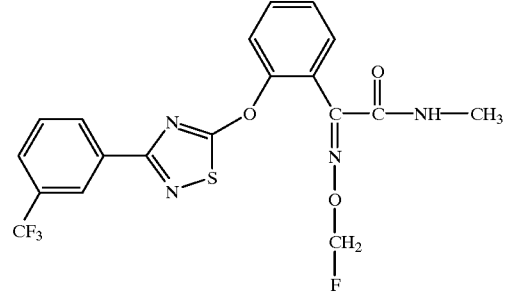<br>(28) | 250 | 100 |
| 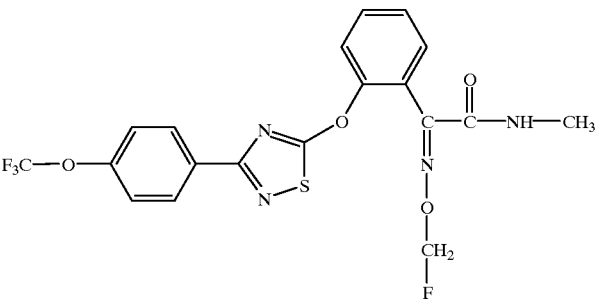<br>(22) | 250 | 100 |
| 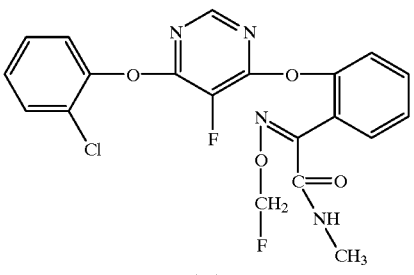<br>(29) | 250 | 100 |

What is claimed is:
1. A compound of the formula (I)

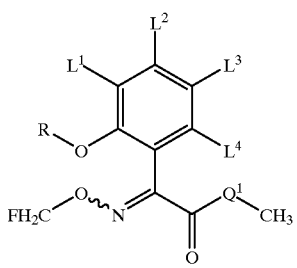
(I)

wherein $Q^1$ represents —NH—,

R represents a moiety selected from the group consisting of

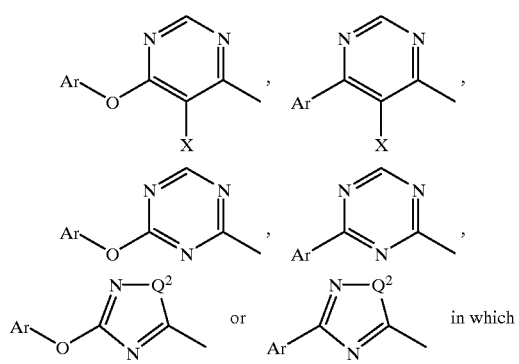

in which

Ar represents phenyl which contains zero to three substituents or naphthyl which contains zero to four substituents, where said substituents are selected from the group consisting of: halogen; cyano; nitro; amino; hydroxyl; mercapto; straight-chain or branched alkyl, alkoxy, alkylthio, alkylsulphinyl or alkylsulphonyl having in each case from 1 to 6 carbon atoms; straight-chain or branched alkenyl, alkenyloxy or alkynyloxy having in each case from 2 to 6 carbon atoms; straight-chain or branched halogenoalkyl, halogenoalkoxy, halogenoalkylthio, halogenoalkylsulphinyl or halogenoalkylsulphonyl having in each case from 1 to 6 carbon atoms and from 1 to 13 identical or different halogen atoms; straight-chain or branched halogenoalkenyl or halogenoalkenyloxy having in each case from 2 to 6 carbon atoms and from 1 to 11 identical or different halogen atoms; straight-chain or branched alkylamino, cycloalkylamino, dialkylamino, alkylcarbonyl, alkylcarbonyloxy, alkoxycarbonyl, alkylsulphonyloxy, hydroximinoalkyl or alkoximinoalkyl having in each case from 1 to 6 carbon atoms in the individual alkyl moieties; doubly attached alkylene or dioxyalkylene having in each case from 1 to 6 carbon atoms and being in each case optionally mono- or polysubstituted by identical or different substituents from the group consisting of halogen, straight-chain or branched alkyl having 1 to 4 carbon atoms and straight-chain or branched halogenoalkyl having 1 to 4 carbon atoms and 1 to 9 identical or different halogen atoms; cycloalkyl, cycloalkenyl, cycloalkoxy or cycloalkenyloxy having in each case 3 to 7 carbon atoms and being in each case substituted by 0 to 4 halogen atoms, and saturated heterocyclyl which is attached via nitrogen, $Q^2$ represents oxygen or sulphur, X represents hydrogen, fluorine, chlorine or bromine and $L^1$, $L^2$, $L^3$ and $L^4$ are identical or different and independently of one another each represents hydrogen; halogen; cyano; nitro; alkyl, alkoxy, alkylthio, alkylsulphinyl or alkylsulphonyl having in each case 1 to 6 carbon atoms and being in each case substituted by 0 to 5 halogen atoms, excluding the following three compounds:

A)
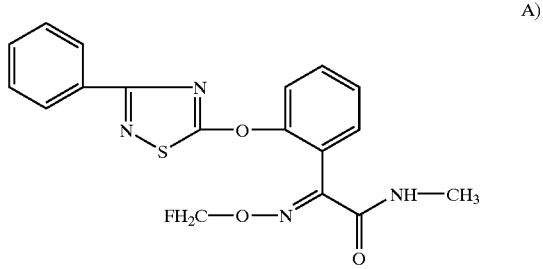

B)
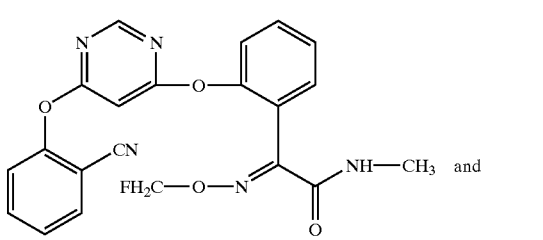
and

C)
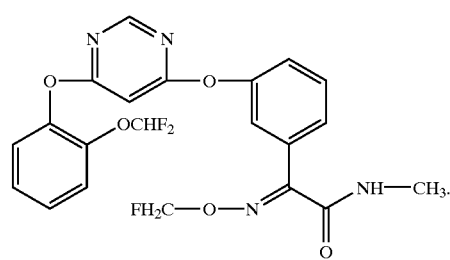

2. The compound of claim 1 wherein $Q^1$ represents —NH—,

R represents a moiety selected from the group consisting of

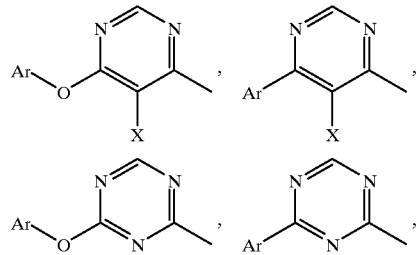

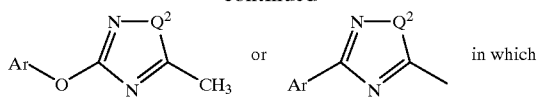 in which

Ar represents phenyl which is contains zero to two identical or different substituents, where said substituents are selected from the group consisting of: fluorine; chlorine; bromine; cyano; nitro; methyl, ethyl, n- or i-propyl, n-, i-, s- or t-butyl; propenyl, but-3-en-2-yl, 2-methyl-propenyl; cyclopropyl; methoxy, ethoxy, n- or i-propoxy, allyloxy; methylthio, ethylthio, n- or i-propylthio; methylsulphinyl, ethylsulphinyl; methylsulphonyl, ethylsulphonyl; trifluoromethyl, trifluoroethyl; difluoromethoxy, trifluoromethoxy, difluorochloromethoxy, trifluoroethoxy; difluoromethylthio, trifluoromethylthio, difluorochloromethylthio; trifluoromethylsulphinyl, trifluoromethylsulphonyl, methoxycarbonyl, ethoxycarbonyl, methoximinomethyl, ethoximinomethyl, methoximinoethyl, ethoximinoethyl; doubly attached propylene, butylene or pentylene; and in each case doubly attached methylenedioxy or ethylenedioxy, each of which is optionally mono- to tetrasubstituted by identical or different substituents from the group consisting of fluorine, chlorine, methyl, trifluoromethyl and ethyl, $Q^2$ represents oxygen or sulphur, X represents hydrogen, fluorine or chlorine and $L^1$, $L^2$, $L^3$ and $L^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. The compound of claim 1 wherein $Q^1$ represents —NH—,

R represents a grouping a or Ar

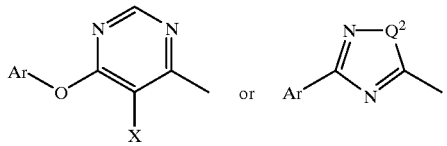

in which

Ar represents phenyl which zero to two identical or different substituents selected from the group consisting of: fluorine, chlorine, bromine, cyano, nitro, methyl, ethyl, n- or i-propyl, n-, i-, s- or t-butyl, but-3-en-2-yl, 2-methylpropenyl, cyclopropyl, methoxy, ethoxy, n- or i-propoxy, allyloxy, methylthio, ethylthio, n- or i-propylthio, trifluoromethyl, trifluoroethyl, difluoromethoxy, trifluoromethoxy, trifluoroethoxy, difluoromethylthio, trifluoromethylthio, methoxycarbonyl, ethoxycarbonyl, methoximinomethyl, ethoximinomethyl, methoximinoethyl, ethoximinoethyl, in each case doubly attached propylene, butylene or pentylene or in each case doubly attached methylenedioxy or ethylenedioxy, each of which contains zero to four identical or different substituents selected from the group consisting of fluorine, chlorine, methyl, trifluoromethyl and ethyl, $Q^2$ represents oxygen or sulphur, X represents hydrogen, fluorine or chlorine and $L^1$ and $L^3$ are identical or different and independently of one another each represents hydrogen or methyl and $L^2$ und $L^4$ represent hydrogen.

4. A pesticidal composition comprising a pesticidally effective amount of at least one compound of claim 1 and an extend.

5. A method for controlling pests, comprising applying from 0.1 to 10,000 g/ha or 0.001 to 50 g of a compound according to claim 1 on said pests and/or their habitat.

6. A process for preparing pesticides, comprising mixing compound according claim 1 with an extender and/or a surfactant.

7. A compound of the formula (II)

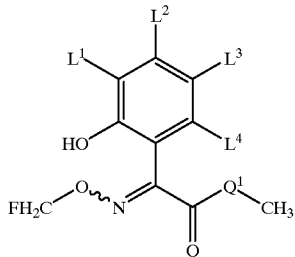

(II)

in which $Q^1$, $L^1$, $L^2$, $L^3$ and $L^4$ are as defined in claim 1.

8. A compound of the formula (IX)

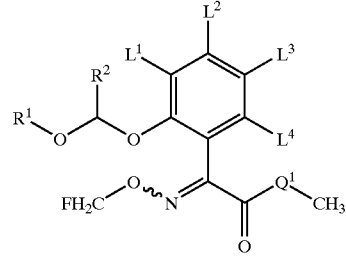

(IX)

in which $R^1$, $R^2$, $L^1$, $L^2$, $L^3$, $L^4$ and $Q^1$ are as defined in claim 1, and $R^1$ represents alkyl, $R^2$ represents hydrogen or alkyl or $R^1$ and $R^2$ together with the atoms to which they are attached represent a five- or six-membered heterocyclic ring.

* * * * *

UNITED STATES PATENT AND TRADEMARK OFFICE
CERTIFICATE OF CORRECTION

PATENT NO. : 6,632,817 B2
DATED : October 14, 2003
INVENTOR(S) : Ulrich Heinemann et al.

It is certified that error appears in the above-identified patent and that said Letters Patent is hereby corrected as shown below:

<u>Title page,</u>
Insert Item:

-- [73] Assignee: Bayer Aktiengesellschaft, Leverkusen (DE) --

Signed and Sealed this

Fourteenth Day of September, 2004

JON W. DUDAS
*Director of the United States Patent and Trademark Office*